United States Patent
Kiening et al.

(10) Patent No.: US 10,437,037 B2
(45) Date of Patent: Oct. 8, 2019

(54) ELECTRONIC MICROSCOPE

(71) Applicant: ARRI Medical GmbH, Munich (DE)

(72) Inventors: Hans Kiening, Lenggries (DE); Peter Geissler, Munich (DE)

(73) Assignee: ARRI MEDICAL GMBH, Munich (DE)

(*) Notice: Subject to any disclaimer, the term of this patent is extended or adjusted under 35 U.S.C. 154(b) by 378 days.

(21) Appl. No.: 15/331,301

(22) Filed: Oct. 21, 2016

(65) Prior Publication Data

US 2017/0115477 A1 Apr. 27, 2017

(30) Foreign Application Priority Data

Oct. 23, 2015 (DE) .................. 10 2015 118 154

(51) Int. Cl.
*G02B 21/36* (2006.01)
*G02B 27/00* (2006.01)
(Continued)

(52) U.S. Cl.
CPC ............ *G02B 21/367* (2013.01); *A61B 90/20* (2016.02); *A61B 90/36* (2016.02); *G02B 3/14* (2013.01); *G02B 21/0012* (2013.01); *G02B 21/02* (2013.01); *G02B 21/22* (2013.01); *G02B 21/241* (2013.01); *G02B 21/244* (2013.01); *G02B 21/365* (2013.01); *G02B 21/368* (2013.01);
(Continued)

(58) Field of Classification Search
USPC .......................................................... 348/80
See application file for complete search history.

(56) References Cited

U.S. PATENT DOCUMENTS 5,835,266 A * 11/1998 Kitajima ............... G02B 7/001
  359/384
6,088,154 A * 7/2000 Morita ............... G02B 21/0012
  359/368

(Continued)

FOREIGN PATENT DOCUMENTS

DE         69919383 T2    12/2005
DE      102005032354 A1    1/2007
(Continued)

*Primary Examiner* — Christopher S Kelley
*Assistant Examiner* — Asmamaw G Tarko
(74) *Attorney, Agent, or Firm* — Amster, Rothstein & Ebenstein LLP

(57) ABSTRACT

An electronic microscope, in particular a surgical microscope, comprises a camera unit that has at least one electronic image sensor for generating primary image data sets and that comprises an imaging optics for generating an image of an object on the image sensor. The microscope further comprises an electronic viewfinder, an adjustment device for varying a focal position of the camera unit, a control device, and a computing device. The control device is adapted to control the adjustment device to make a cyclically repeating variation of the focal position of the camera unit between a plurality of focal values and to control the image sensor to generate a respective primary image data set for each of the plurality of focal values. The computing device is adapted to determine a secondary image data set from the primary image data sets generated for the plurality of focal values, said secondary image data set having an extended depth of field relative to the respective primary image data sets.

18 Claims, 2 Drawing Sheets

Figure 1:
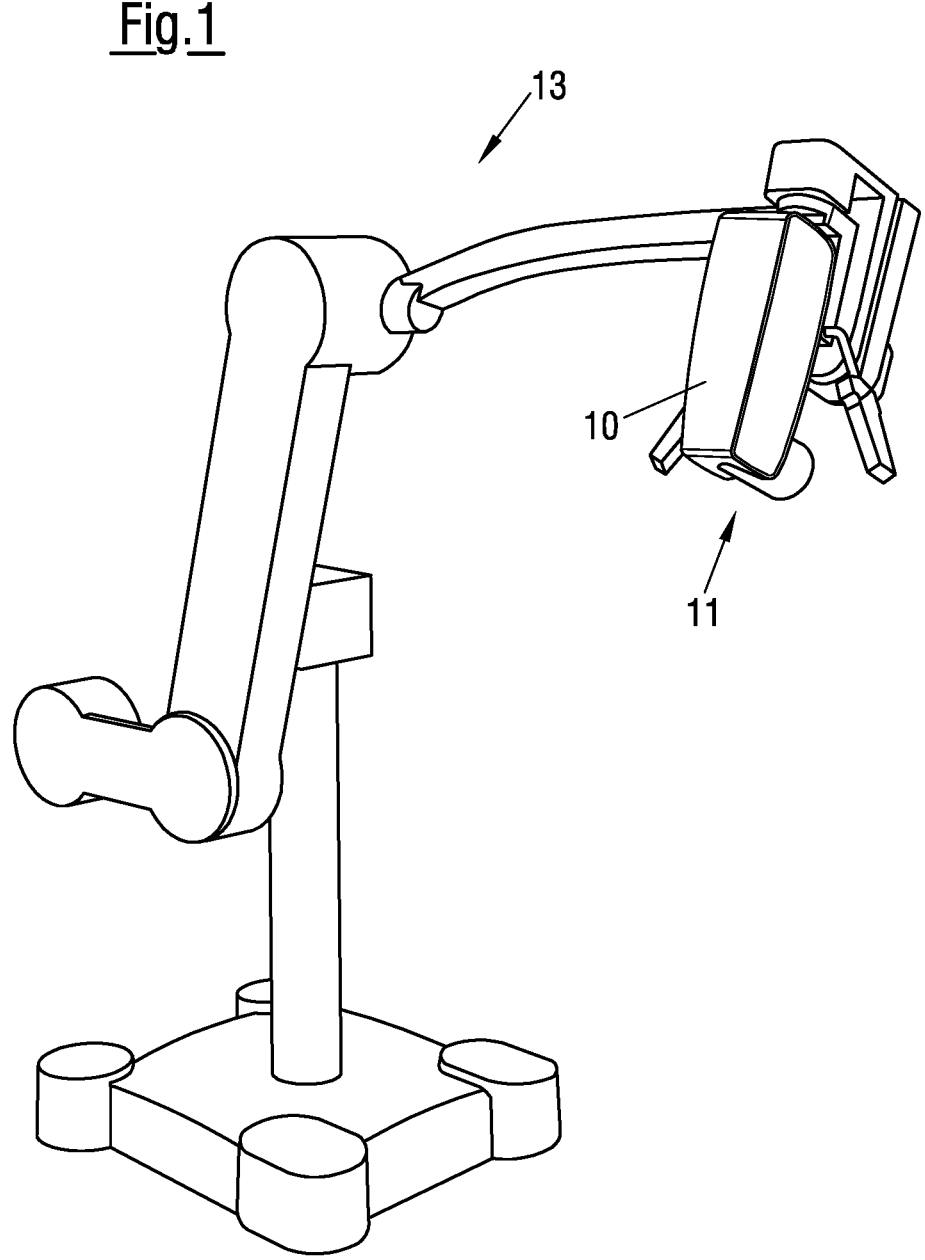

(51) Int. Cl.
*G02B 21/00* (2006.01)
*G02B 21/22* (2006.01)
*G02B 21/24* (2006.01)
*G06T 5/50* (2006.01)
*G02B 3/14* (2006.01)
*G02B 21/02* (2006.01)
*G06T 5/00* (2006.01)
*A61B 90/00* (2016.01)
*A61B 90/20* (2016.01)

(52) U.S. Cl.
CPC .......... *G02B 27/0075* (2013.01); *G06T 5/003* (2013.01); *G06T 5/50* (2013.01); *G06T 2207/10056* (2013.01); *G06T 2207/10148* (2013.01)

(56) References Cited

U.S. PATENT DOCUMENTS

| | | | | |
|---|---|---|---|---|
| 6,266,182 | B1 * | 7/2001 | Morita | G02B 21/0012 359/368 |
| 6,396,627 | B1 * | 5/2002 | Tachihara | G02B 21/22 348/42 |
| 6,449,087 | B2 * | 9/2002 | Ogino | G02B 21/0056 250/201.3 |
| 6,634,749 | B1 * | 10/2003 | Morrison | A61B 3/113 351/209 |
| 9,488,817 | B2 * | 11/2016 | Shi | G02B 21/02 |
| 2004/0264765 | A1 * | 12/2004 | Ohba | G02B 21/22 382/154 |
| 2011/0025880 | A1 * | 2/2011 | Nandy | G01N 21/6458 348/226.1 |
| 2012/0281132 | A1 * | 11/2012 | Ogura | H04N 5/23212 348/348 |
| 2014/0327742 | A1 * | 11/2014 | Kiening | G02B 21/22 348/46 |
| 2015/0145980 | A1 | 5/2015 | Bryll | |
| 2015/0178980 | A1 | 6/2015 | Bublitz et al. | |
| 2015/0216411 | A1 * | 8/2015 | Gaton | A61B 3/1035 351/206 |
| 2017/0111581 | A1 * | 4/2017 | Muenzenmayer | G02B 21/367 |

FOREIGN PATENT DOCUMENTS

| | | | | |
|---|---|---|---|---|
| DE | 102005032354 B | * | 1/2007 | ......... G02B 27/0075 |
| DE | 102012212801 A1 | | 1/2014 | |
| DE | 102012218863 A1 | | 4/2014 | |
| DE | 102013208306 A1 | | 11/2014 | |
| DE | 102014223387 A1 | | 5/2015 | |
| WO | 9417493 A1 | | 8/1994 | |
| WO | 2014060412 A1 | | 4/2014 | |

* cited by examiner

ELECTRONIC MICROSCOPE

The present invention relates to an electronic microscope, in particular to a surgical microscope, having a camera unit that comprises at least one electronic image sensor for generating image data sets and that comprises an imaging optics for generating an image of an object, in particular of a surgical site, on the image sensor. A electronic viewfinder is provided at the microscope to display those images which correspond to the generated image data sets.

Such electronic microscopes are used by a surgeon, for example, to carry out an operation using the advantages of an optical magnification of the surgical site effected by the microscope. In this respect, the surgeon observes or monitors the surgical site at least at times only via the electronic viewfinder (e.g. two small-format monitors having two eyepieces placed on) on which the image information detected by the image sensor(s) are reproduced visually and in particular dynamically in real time. Electronic stereo microscopes are used in this respect such as are known from WO 2014/060412 A1 and US 2014/0327742 A1.

The demands on the image sensor and on the imaging optics of the microscope can in particular be contradictory in the medical field of application: On the one hand, a large image sensor and a large aperture of the imaging optics are desirable to achieve a high optical sensitivity of the microscope and to be able to use relatively low illumination that does not unnecessarily heat up body tissue. On the other hand, depending on the area of application and in particular for short focal lengths (i.e. in the wide angle range), a larger depth of field can be desired (i.e. a larger depth range that is imaged in focus) to clearly resolve structures at different distances from the microscope. This demand could be satisfied by a smaller aperture that is, however, not desired since then higher illumination would in turn be necessary.

It is an object of the invention to provide an improved electronic microscope that can detect and display images with a greater depth of field without the aperture of the imaging optics having to be reduced for this purpose.

The object is satisfied in that the microscope has (i) an adjustment device for varying a focal position of the camera unit; (ii) a control device; and (iii) a computing device, with the control device being adapted to control the adjustment device to make a cyclically repeating variation of the focal position of the camera unit between a plurality of focal values and to control the image sensor(s) to generate a respective primary image data set for each of the plurality of focal values. The computing device is adapted to determine a secondary image data set from the primary image data sets generated for the plurality of focal values, said secondary image data set having an extended depth of field relative to the respective primary image data sets. The electronic viewfinder is adapted to display an image corresponding to the secondary image data set.

The invention is based on the recognition that with a microscope, at least in some applications, no fast movement paths have to be observed and also no fast movements of the camera unit or of its imaging optics (e.g. panning shots) have to be carried out. There is hereby the possibility of detecting a plurality of (primary) images for different focal positions (i.e. having a different position of the focal plane in the object space) in sequence and in particular in real time in a respective secondary image determination cycle and to combine them to form a single (secondary) image with increased depth of field and to display them at the electronic viewfinder. This procedure is in particular especially advantageous on a use of the microscope as a surgical microscope since in this application a large depth of field range is desired as a rule without an aperture of the imaging optics being greatly reduced in an unwanted manner for this purpose, which would have to be compensated by an increased illumination intensity. At the same time, a surgical site frequently represents a comparatively static scene that is only subject to small time changes. These small time changes are utilized for a technical image processing generation of a synthetic image having an extended depth of field that is composed of a plurality of real images of the scene (having a respective different depth of field or working distance).

The control device and the computing device distinguished by their terms in connection with the invention can be formed by a common unit. The number of individual components of the microscope is hereby reduced.

It must furthermore be noted in connection with the invention that, on a configuration of the electronic microscope as a stereo microscope, the generation of the primary image data sets and the determination of a respective secondary image data set can be carried out within a cycle both for a right channel and for a left channel, as will be explained in the following.

In accordance with an embodiment, the adjustment device is formed from an electrical, electromagnetic, electromotoric or piezoelectric device. A simple and fast control is hereby possible.

To be able to vary the focal position of the camera unit, the imaging optics can, for example, have at least one lens that is movable by means of the adjustment device along an optical axis of the imaging optics.

Alternatively or additionally, the imaging optics has at least one lens whose focal length or refractive power is variable by means of the adjustment device to vary the focal position of the camera unit.

The lens can in particular be configured as a liquid lens to be able to vary the focal position particularly quickly. In this case, the adjustment device is e.g. configured as an electrode arrangement such that an electrical field can be applied to the lens by means of a ring electrode, preferably two ring electrodes, arranged around the lens, with the focal length or the refractive power of the lens being variable in dependence on the strength of the electrical field.

In accordance with a further embodiment, the image sensor is movable by means of the adjustment device along an optical axis of the imaging optics to vary the focal position of the camera unit. This embodiment can in particular be pursued alternatively to the previous case of an adjustment device cooperating with the imaging optics, e.g. when the imaging optics is to be configured as particularly compact or encapsulated.

The adjustment device can comprise one or more actuators. The adjustment device can in particular comprise actuators of camera units familiar to the skilled person, e.g. for adjusting an aperture of the imaging optics.

The camera unit and in particular its imaging optics can have a depth of field range for each of the plurality of focal values set in a cycle, with the focal positions of the camera unit corresponding to the plurality of focal values being selected such that the depth of field ranges of the plurality of focal values overlap pair-wise. The primary image data sets generated for the different focal values can hereby be combined particularly easily to form a secondary image data set having a continuously extended depth of field.

The focal positions of the camera unit corresponding to the set plurality of focal values can in particular respectively differ from one another by a distance that at least substantially corresponds to half the respective depth of field range (i.e. of the depth of field range of a respective focal value). A corresponding mutual overlap of the depth of field ranges of the plurality of focal values set after one another can e.g. be utilized to compensate variations within a respective depth of field range of a primary image data set or between the primary image data sets so that the effective depth of field range of the determined secondary image is particularly homogeneous.

The above statements on the depth of field ranges and on the mutual distances generally relate to an observation along an optical axis of the imaging optics.

In accordance with a preferred embodiment, the control device is adapted to control the adjustment device to make a cyclically repeating variation of the focal position of the camera unit between at least three different focal values and to control the image sensor to generate a respective primary image data set for each of the at least three focal values. The computing device is in this respect adapted to determine a secondary image data set from the primary image data sets generated for the at least three focal values, said secondary image data set having an extended depth of field relative to the respective primary image data sets. A sufficiently large and homogeneous depth of field can be achieved by the generation and exploitation of three different primary image data sets per secondary image determination cycle and an operation and in particular a reproduction of the secondary images in the electronic viewfinder are nevertheless still possible in real time or almost in real time.

In addition to the cyclically repeating variation of the focal position of the camera unit, the focal position of the camera unit for the plurality of focal values can also be variable together. It is hereby possible to vary the working distance of the microscope (distance between the imaging optics and the object to be imaged), with an associated adaptation of the focal position of the camera unit being superposed with the cyclically repeating variation of the focal position. In accordance with a particularly advantageous embodiment, this can be done by means of the same adjustment device. In this case, both the cyclic running through of the different focal positions for the purpose of generating the different primary image data sets and the (optionally superposed) general adjustment of the working distance of the microscope can therefore take place by means of the same adjustment device without a plurality of different adjustment devices being required for this purpose.

In accordance with a further embodiment, the imaging optics has a variable magnification factor (i.e. imaging scale, zoom factor), with the control device being adapted to control the adjustment device to make a cyclically repeating variation of the focal position of the camera unit for the same magnification factor. In other words, the generation of the primary image data sets for the different focal positions can nevertheless take place with an unchanged magnification factor even with an imaging optics having a variable magnification factor.

To determine the secondary image data set, the computing device is preferably adapted to divide the primary image data sets generated for the plurality of focal values into a plurality of image zones and to evaluate them within the image zones with respect to a respective degree of sharpness and to determine the secondary image data set in that the data of the primary image data set having the highest degree of sharpness for each of the plurality of image zones is selected. In other words, the secondary image data set is composed of the data selected for the different image zones on the basis of the criterion of maximum sharpness.

Depending on the image sensor type, a respective image zone can comprise a group of a plurality of spatially adjacent picture elements (pixels) of the same color or of different colors. The consideration of picture elements of the same color is in particular of advantage when the image sensor has sensor elements of three different colors that are arranged in accordance with the scheme of a color mosaic filter, preferably a so-called Bayer filter. In such a case, every color does not necessarily have to be considered, but it may rather be sufficient for the determination of the respective degree of sharpness only to compare and/or offset the picture elements of a single color (preferably green) with one another, with the picture elements of the further colors being treated exactly as the adjacent picture elements of the actually considered color without any further examination. The named respective image zone can in an extreme case also be formed by a single picture element or by only two picture elements. A plurality of image zones are, however, always provided, i.e. the (secondary) image is composed of a plurality of image zones or of the secondary image data determined for a plurality of image zones.

The observed image elements can be directly or indirectly adjacent. The latter is in particular the case when only the image data of picture elements of the same respective color are used—as explained—with an image sensor with a color mosaic filter. The respective image zone, however, comprises a spatial environment of picture elements that allows a determination by calculation and also a visual perception of a degree of sharpness.

The computation device can be adapted to evaluate the primary image data sets with respect to the degree of sharpness in that at least one difference or at least one quotient between the image data of at least two adjacent picture elements (i.e. between the respective picture element values) is formed for the respective image zone based on the respective primary image data set (and in particular for the picture elements of the same color). The greater the difference or the quotient, the greater the degree of sharpness generally is. It is thus in particular possible for the determination of the secondary image data set that the data of the primary image data set having the greatest difference or having the largest quotient between the picture element values are selected for each of the different image zones. In this respect, a plurality of differences or quotients can also be formed for a respective image zone, with the values hereby generated being able to be averaged, for example, to determine a degree of sharpness.

An absolute difference or a standardized difference can be formed, i.e. the difference is divided by an absolute value.

The mutual offsetting of the observed picture elements or picture zones does not have to take place linearly, but can also take place at a higher order. The observed picture elements can furthermore be adjacent to one another (e.g. horizontally and/or vertically) in a single direction or in a plurality of directions.

In accordance with a further embodiment, the control device, the computing device and the electronic viewfinder are synchronized with one another and are adapted to carry out the generation of the primary image data set for the plurality of focal values of a cycle;

the determination of the respective secondary image data set; and the display of the respective (secondary) image at a frequency that amounts to at least 25 Hz. It is hereby ensured that the image corresponding to the secondary image data set can be displayed to the user of the microscope via the electronic viewfinder at least subjectively substantially continuously ("jerk-free") and with as little delay as possible.

The electronic microscope is preferably configured as a stereo microscope, with the control device being adapted to control the at least one image sensor to generate a respective primary image data set of a right channel and of a left channel for each of the plurality of focal values. The stereoscopic image data sets can generally either be generated by means of a single image sensor, in particular in that the object is imaged alternating in time onto the image sensor by means of a left and a right part optical path or in that the two images corresponding to the right channel and to the left channel are simultaneously generated next to one another on the image sensor. Or the microscope comprises two image sensors, with the image corresponding to the right channel always being generated on the one image sensor and the image corresponding to the left channel always being generated on the other image sensor by means of corresponding part optical paths, and with the two image sensors simultaneously generating the stereoscopic image data sets.

In the embodiment as a stereo microscope, the computing device is furthermore preferably adapted to determine a respective secondary image data set of the right channel and of the left channel from the primary image data sets generated for the plurality of focal values, said secondary image data set having an expanded depth of field relative to the respective primary image data sets. The electronic viewfinder is in this respect adapted to display a respective image of the right channel and of the left channel corresponding to the respective secondary image data set. The above-explained measures are thus carried out at least partly in parallel for two stereo channels such that stereoscopic (secondary) images can be displayed at the electronic viewfinder.

In general in this respect, the division into image zones and the selection of the respective focal position or of the respective primary image data set can take place in an identical manner for the two stereo channels (right and left). In this respect, the explained selection of a respective primary image data set can be carried out in parallel and independently of one another for the two stereo channels.

It is, however, possible in accordance with a particularly advantageous embodiment only to carry out the determination of a degree of sharpness and the corresponding selection of the respective primary image data set for one of the two stereo channels and to use the selection result automatically also for the other of the two stereo channels. The computing device can in particular be adapted to determine the respective secondary image data set of the right channel and of the left channel
  in that the primary image data sets of the right channel and the primary image date sets of the left channel are divided into a plurality of image zones corresponding to one another (i.e. being at least substantially congruent) with respect to the two channels;
  in that the primary image data sets generated for the plurality of focal values are evaluated within each image zone for only one of the two channels (i.e. only for the right channel or only for the left channel) with respect to the respective degree of sharpness, with the focal value having the highest degree of sharpness being identified with respect to each image zone (in particular in the manner already explained, e.g. by formation and mutual comparison of difference values); and
  in that the respective secondary image data set is determined for both the right channel and the left channel by selecting for each image zone the respective data of that primary image data set that corresponds to the focal value which has been identified for the only one of the two channels.

In other words, a substantial part of the analysis (determining the degree of sharpness and corresponding selection of the focal value or of the focal position) is only carried out for one of the two stereo channels, with the result also being used for the other one of the two stereo channels. The calculation effort can hereby be minimized and a faster processing of the image data can also be achieved. This is also in particular of advantage for a reproduction of the (secondary) images at the electronic viewfinder that is as smooth and is free of delay as possible.

The electronic viewfinder can in particular have two electronic display devices or one electronic display device divided into two display zones, with the electronic viewfinder being adapted to display the respective (secondary) image of the right channel and of the left channel at the two display devices or two display zones. The images of the right channel and of the left channel can be observed by the user of the microscope via a respectively associated eyepiece, with the image of the right channel being supplied only to the right eye and the image of the left channel only being supplied to the left eye.

In accordance with a particularly advantageous embodiment, the electronic microscope can selectively be operated in a first operating mode of expanded depth of field or in a second operating mode of increased temporal resolution. In the first operating mode, the secondary image data sets are determined—as explained in detail above—from the primary image data sets generated for the plurality of focal values and are displayed (optionally stereoscopically) at the electronic viewfinder as a (secondary) image. In the second operating mode, the control device is adapted to control the image sensor or sensors for generating primary image data sets without controlling the adjustment device to make a cyclically repeating variation of the focal position of the camera unit between the plurality of focal values. In other words, in the second operating mode, passing through a plurality of focal positions to increase the depth of field is dispensed with in favor of a faster image generation. In this respect, the electronic viewfinder is adapted to display a (primary) image corresponding to the respective primary image data set. In this embodiment, the user can therefore selectively base the operation of the microscope either on an expanded depth of field or on an increased temporal resolution, with a fast switchover between the two operating modes being able to be provided. It is furthermore also conceivable to provide a gradual adjustment of these mutually competing operating criteria (e.g. having a variable number of focal values and corresponding primary image data sets that are set or evaluated per cycle).

The invention will be described in the following only by way of example with reference to an embodiment. There are shown:
  FIG. 1 a perspective view of a microscope with stand; and
  FIG. 2 a schematic longitudinal sectional view of a microscope.

FIG. 1 shows an electronic stereoscopic microscope 10 in an application as a surgical microscope. The microscope 10 comprises a camera unit 11 that is fastened to a multiaxially pivotable stand 13 and that is angled in the embodiment shown as is known from WO 2014/060412 A1 and US 2014/0327742 A1. The microscope 10 furthermore comprises an electronic viewfinder (not shown in FIG. 1) associated with the camera unit 11. Such a microscope 10 is used, for example, in surgical interventions in the field of clinical medicine.

Figure 2:
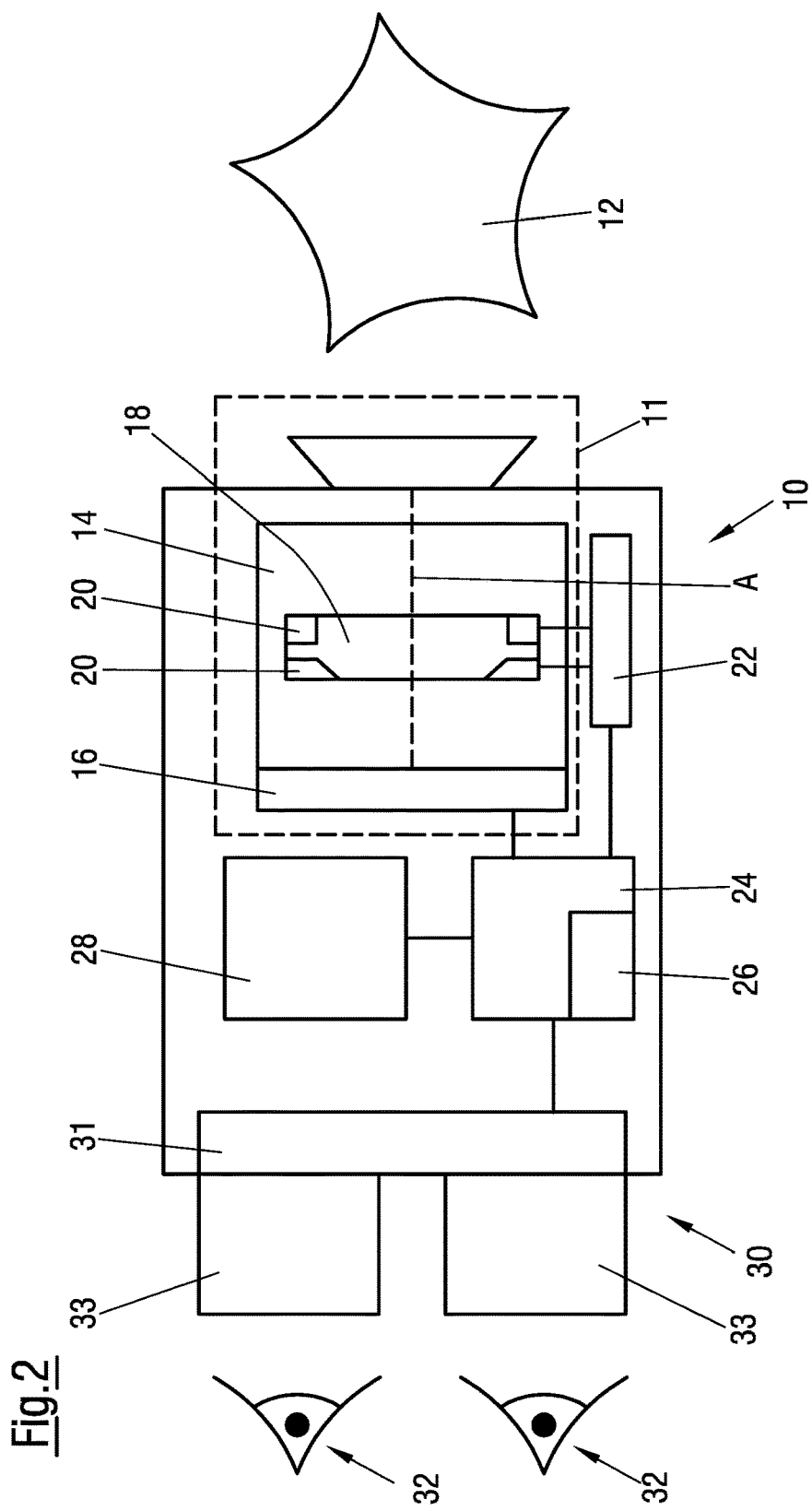

FIG. 2 shows details of such an electronic microscope 10 in a straight-axis design, with a single (i.e. monoscopic) optical path being shown for the purpose of a simpler representation. The microscope 10 has an imaging optics 14 having an optical axis A at the camera unit 11 for the optical detection of a surgical site 12 and has at least one electronic image sensor 16 that comprises a plurality of light-sensitive sensor elements in a two-dimensional arrangement. The imaging optics 14 comprises a liquid lens 18 whose focal length is variably adjustable. An adjustment device 22 is provided for this purpose that has two electrodes 20 running around the liquid lens 18. An electrical field can be generated via the electrodes 20 that effects a desired adjustment of the focal length of the liquid lens 18.

In a stereoscopic embodiment not shown here, the microscope 10 comprises a second optical path of the same kind to provide a second channel and thus to be able to generate respective primary image data sets of a right channel and of a left channel. The optical paths of the right channel and of the left channel can have separate components or at least partly identical components (e.g. common optical elements, a common adjustment device 22, and/or a common image sensor 16), with a common adjustment device 22 preferably being provided for varying the focal position of the two channels of the camera unit 11.

The adjustment device 22 is controlled by a control device 24 connected to the adjustment device 22. The control device 24 furthermore serves for the control of the image sensor 16, of a computing device 28, and of an electronic viewfinder 30 of the microscope 10. The electronic viewfinder 30 comprises a electronic display device 31 divided into two as well as two eyepieces 33 placed onto the display device 31. Configuration data of the microscope 10 are stored in a memory 26 of the control device 24 that simultaneously serves as an image data store.

In an operating mode of expanded depth of field of the microscope 10, the control device 24 controls the adjustment device 22 in dependence on the configuration data stored in the memory 26 in a fast sequence to make a cyclically repeating variation of the focal position of the imaging optics 14 in accordance with a plurality of different focal length values of the liquid lens 18. The control device 24 controls the image sensor 16 for each focal position set in accordance with the plurality of focal length values to generate a respective associated primary image data set that is stored in the memory 26 of the control device 24.

On completion of a respective cycle, the computing device 28 determines a secondary image data set that has an expanded depth of field relative to the respective primary image data sets—as already explained above—from the primary image data sets generated in the course of a cycle. The image corresponding to the determined secondary image data set is displayed at the electronic viewfinder 30 and is to be observed through the eyepieces 33 by a pair of human eyes 32 of a user of the microscope 10 not shown in any more detail. The displayed image allows the user to track the surgical site 12 "live" without any significant time delay and with a greater depth of field. By use of the microscope 10, the surgical site 12 can be shown with a desired magnification. A surgeon can therefore carry out the operation with high precision and with low fatigue.

REFERENCE NUMERAL LIST 10 microscope
11 camera unit
13 stand
12 surgical site
14 imaging optics
16 image sensor
18 liquid lens
20 electrode
22 adjustment device
24 control device
26 memory
28 computing device
30 viewfinder
31 display device
32 eye
33 eyepiece
A optical axis

The invention claimed is:

1. An electronic microscope (10),
    having a camera unit (11) that comprises at least one electronic image sensor (16) for generating primary image data sets and that comprises an imaging optics (14) for generating an image of an object (12) on the image sensor (16);
    an electronic viewfinder (30);
    an adjustment device (22) for varying a focal position of the camera unit (11);
    a control device (24); and
    a computing device (28),
    wherein the control device (24) is adapted to control the adjustment device (22) to make a cyclically repeating variation of the focal position of the camera unit (11) between a plurality of focal values and to control the image sensor (16) to generate a respective primary image data set for each of the plurality of focal values;
    wherein the computing device (28) is adapted to determine a secondary image data set from the primary image data sets generated for the plurality of focal values, said secondary image data set having an extended depth of field relative to the respective primary image data sets;
    wherein the focal positions corresponding to the plurality of focal values differ by a distance that at least substantially corresponds to half the respective depth of field zone; and
    wherein the electronic viewfinder (30) is adapted to display an image corresponding to the secondary image data set.

2. An electronic microscope (10) in accordance with claim 1,
    wherein the adjustment device (22) is configured as an electrical, electromagnetic, electromotoric or piezoelectric device.

3. An electronic microscope (10) in accordance with claim 1,
    wherein the imaging optics (14) has at least one lens (18) that is movable along an optical axis (A) of the imaging optics (14) by means of the adjustment device (22) to vary the focal position of the camera unit (11).

4. An electronic microscope (10) in accordance with claim 1,
    wherein the imaging optics (14) has at least one lens (18) whose focal length is variable by means of the adjustment device (22) to vary the focal position of the camera unit (11).

5. An electronic microscope (10) in accordance with claim 4,
    wherein the lens is configured as a liquid lens (18).

6. An electronic microscope (10) in accordance with claim 1,
wherein the image sensor (16) is movable along an optical axis (A) of the imaging optics (14) by means of the adjustment device (22) to vary the focal position of the camera unit (11).

7. An electronic microscope (10) in accordance with claim 1,
wherein the camera unit (11) has a depth of field zone for each of the plurality of focal values, with the focal positions corresponding to the plurality of focal values being selected such that the depth of field zones of the plurality of focal values overlap pair-wise.

8. An electronic microscope (10) in accordance with claim 1,
wherein the control device (24) is adapted to control the adjustment device (22) to make a cyclically repeating variation of the focal position of the camera unit (11) between at least three focal values and to control the image sensor to generate a respective primary image data set for each of the at least three focal values;
wherein the computing device (28) is adapted to determine a secondary image data set from the primary image data sets generated for the at least three focal values, said secondary image data set having an extended depth of field relative to the respective primary image data sets.

9. An electronic microscope (10) in accordance with claim 1,
wherein, in addition to the cyclically repeating variation of the focal position of the camera unit (11), the focal position of the camera unit (11) for the plurality of focal values can also be varied together.

10. An electronic microscope (10) in accordance with claim 1,
wherein the imaging optics (14) has a variable magnification factor, with the control device (24) being adapted to control the adjustment device (22) to make the cyclically repeating variation of the focal position of the camera unit (11) for the same magnification factor.

11. An electronic microscope (10) in accordance with claim 1,
wherein the computing device (28) is adapted to divide the primary image data sets generated for the plurality of focal values into a plurality of image zones and to evaluate them within the image zones with respect to a respective degree of sharpness and to determine the secondary image data set in that the data of the primary image data set having the highest degree of sharpness for each of the plurality of image zones are selected.

12. An electronic microscope (10) in accordance with claim 11,
wherein the computing device (28) is adapted to evaluate the primary image data sets with respect to the degree of sharpness such that at least one difference or at least one quotient is formed between the image data of at least two adjacent picture elements for the respective image zone on the basis of the respective primary image data set.

13. An electronic microscope (10) in accordance with claim 1,
wherein the control device (24), the computing device (28) and the electronic viewfinder (30) are synchronized with one another and are adapted
to generate the primary image data set for the plurality of focal values of a cycle;
to determine the respective secondary image data set; and
to display the respective image
at a frequency that amounts to at least 25 Hz.

14. An electronic microscope (10) in accordance with claim 1,
wherein the electronic microscope (10) is configured as a stereo microscope, with the control device (24) being adapted to control the at least one image sensor (16) to generate a respective primary image data set of a right channel and of a left channel for each of the plurality of focal values;
wherein the computing device (38) is adapted to determine a respective secondary image data set of the right channel and of the left channel from the primary image data sets generated for the plurality of focal values, said secondary image data set having an expanded depth of field relative to the respective primary image data sets; and
wherein the electronic viewfinder (30) is adapted to display a respective image of the right channel and of the left channel corresponding to the respective secondary image data set.

15. An electronic microscope (10) in accordance with claim 14, wherein the computing device (28) is adapted to determine the respective secondary image data set of the right channel and of the left channel in that
the primary image data sets of the right channel and the primary image date sets of the left channel are divided into a plurality of image zones corresponding to one another with respect to the two channels;
the primary image data sets generated for the plurality of focal values are evaluated within each image zone for only one of the two channels with respect to a respective degree of sharpness, with the focal value having the highest degree of sharpness being identified;
and the respective secondary image data set for both the right channel and the left channel is determined by selecting for the plurality of image zones the data of that primary image data set that corresponds to the respective focal value identified for the one of the two channels.

16. An electronic microscope (10) in accordance with claim 15,
wherein the electronic viewfinder (30) has two electronic display devices (31), with the electronic viewfinder (30) being adapted to display the respective image of the right channel and of the left channel at the two display devices (31).

17. An electronic microscope (10) in accordance with claim 15,
wherein the electronic viewfinder (30) has an electronic display device (31) divided into two display zones, with the electronic viewfinder (30) being adapted to display the respective image of the right channel and of the left channel at the two display zones.

18. An electronic microscope (10) in accordance with claim 1,
wherein the electronic microscope (10) can selectively be operable in a first operating mode of expanded depth of field or in a second operating mode of increased temporal resolution;
wherein, in the first operating mode, the secondary image data sets are determined from the primary image data sets generated for the plurality of focal values and are displayed at the electronic viewfinder (30); and
wherein, in the second operating mode, the control device (24) is adapted to control the image sensor (16) to generate primary image data sets without controlling the adjustment device (22) to make a cyclically repeating variation of the focal position of the camera unit between the plurality of focal values, and the electronic viewfinder (30) is adapted to display an image corresponding to the respective primary image data set.

* * * * *